United States Patent
Kim et al.

(10) Patent No.: US 9,089,843 B2
(45) Date of Patent: Jul. 28, 2015

(54) FLUID CONTROLLING APPARATUS AND FILTER AND BIOCHIP INCLUDING THE FLUID CONTROLLING APPARATUS

(75) Inventors: Minseok S. Kim, Yongin-si (KR); Sun-soo Kim, Suwon-si (KR); Jin-hoon Kim, Suwon-si (KR); Won-ho Lee, Suwon-si (KR); Jeong-gun Lee, Seoul (KR); Tae-seok Sim, Seoul (KR); Sang-hyun Baek, Hwaseong-si (KR); Hyo-young Jeong, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 13/584,552

(22) Filed: Aug. 13, 2012

(65) Prior Publication Data

US 2013/0079248 A1   Mar. 28, 2013

(30) Foreign Application Priority Data

Sep. 26, 2011 (KR) .................. 10-2011-0096983

(51) Int. Cl.
| | |
|---|---|
| B01D 29/50 | (2006.01) |
| C40B 40/00 | (2006.01) |
| C40B 40/06 | (2006.01) |
| C40B 40/10 | (2006.01) |
| C40B 40/12 | (2006.01) |
| C40B 60/00 | (2006.01) |
| B01L 3/00 | (2006.01) |
| G01N 21/05 | (2006.01) |
| G01N 21/03 | (2006.01) |
| G01N 1/40 | (2006.01) |

(52) U.S. Cl.
CPC ..... *B01L 3/502753* (2013.01); *B01L 3/502746* (2013.01); *G01N 21/05* (2013.01); *B01L 2200/10* (2013.01); *B01L 2300/0816* (2013.01); *B01L 2300/0819* (2013.01); *B01L 2300/0877* (2013.01); *B01L 2300/0887* (2013.01); *B01L 2400/0487* (2013.01); *B01L 2400/086* (2013.01); *G01N 2001/4088* (2013.01); *G01N 2021/0325* (2013.01); *G01N 2021/0346* (2013.01)

(58) Field of Classification Search
USPC ................... 506/13, 33; 422/502; 435/289.1; 436/177
See application file for complete search history.

(56) References Cited

U.S. PATENT DOCUMENTS

| | | | |
|---|---|---|---|
| 6,156,270 A | 12/2000 | Buechler | |
| 6,887,693 B2 * | 5/2005 | McMillan et al. | 435/173.7 |
| 6,900,021 B1 * | 5/2005 | Harrison et al. | 435/7.21 |
| 8,372,656 B2 * | 2/2013 | Kim et al. | 436/177 |

(Continued)

FOREIGN PATENT DOCUMENTS

| | | |
|---|---|---|
| EP | 1531003 A1 | 5/2005 |
| EP | 2460589 A1 | 6/2012 |

OTHER PUBLICATIONS

European Patent Office, Extended European Search Report in European Application No. 12185817.9 (Feb. 27, 2013).

(Continued)

*Primary Examiner* — Samuel Woolwine
*Assistant Examiner* — Kaijiang Zhang
(74) *Attorney, Agent, or Firm* — Leydig, Voit & Mayer, Ltd.

(57) ABSTRACT

A fluid controlling apparatus including an inlet through which a fluid is introduced, a channel portion connected to the inlet, an outlet that is connected to the channel portion and through which the fluid is discharged, and at least one fluid resisting portion disposed between the inlet and the outlet, as well as a filter and a biochip including the fluid controlling apparatus.

13 Claims, 9 Drawing Sheets
(3 of 9 Drawing Sheet(s) Filed in Color)

(56) References Cited

U.S. PATENT DOCUMENTS

2002/0039783 A1 4/2002 McMillan et al.
2005/0106756 A1* 5/2005 Blankenstein et al. ....... 436/523
2005/0245887 A1* 11/2005 Olsen et al. ................... 604/284
2006/0011480 A1 1/2006 Sano et al.

OTHER PUBLICATIONS

Gilbert et al., "Computational and Functional Evaluation of a Microfluidic Blood Flow Device," *American Society of Artificial Internal Organs Journal*, 2007, 53, 447-455.

Saias et al., "Design, Modeling and Characterization of Microfluidic Architectures for High Flow Rate, Small Footprint Microfluidic Systems," *Lab Chip*, 2011, 11, 822.

Chung et al., "Effect of Geometry on Fluid Mixing of the Rhombic Micromixers," *Microfluid Nanofluid*, 2008, 4, 419-425.

Saias et al., "Microfluidic Magnetic Cell Sorting System for Cancer Diagnosis," *Twelfth International Conference on Miniaturized Systems for Chemistry and Life Sciences*, Oct. 12-16, 2008, San Diego, California, USA.

* cited by examiner

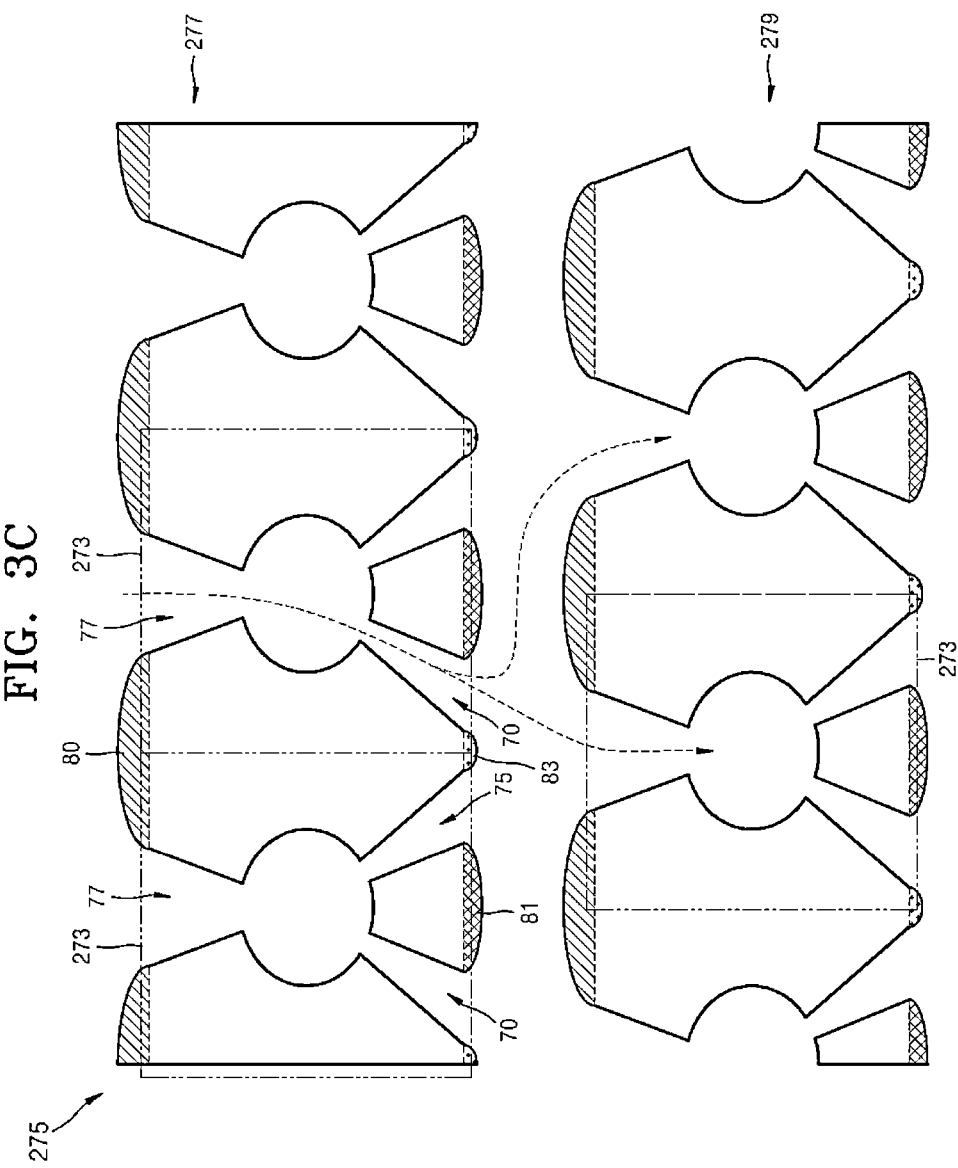

FLUID CONTROLLING APPARATUS AND FILTER AND BIOCHIP INCLUDING THE FLUID CONTROLLING APPARATUS

CROSS-REFERENCE TO RELATED APPLICATIONS

This application claims the benefit of Korean Patent Application No. 10-2011-0096983, filed on Sep. 26, 2011, in the Korean Intellectual Property Office, the disclosure of which is incorporated herein in its entirety by reference.

COLOR DRAWINGS

The patent or application file contains at least one drawing executed in color. Copies of this patent or patent application publication with color drawing(s) will be provided by the Office upon request and payment of the necessary fee.

BACKGROUND

1. Field

The present disclosure relates to fluid controlling apparatuses, and filters and bio-chips including the fluid controlling apparatuses. More particularly, the present disclosure relates to a fluid controlling apparatus including a fluid resisting unit to control a speed of a fluid and a filter, and a biochip both including the fluid controlling apparatus.

2. Description of the Related Art

Microfluidic devices are used to perform biological or chemical reactions by manipulating a small amount of fluid. Microfluidic devices may include microfluidic structures arranged within any of variously shaped platforms, such as a chip or a disc. A microfluidic structure may include, for example, a chamber that stores a fluid, a channel through which the fluid flows, and a valve that controls fluid flow. The chamber, channel, and valve may be disposed in various combinations within a platform. A hydrodynamic filter is a system for capturing target materials included in a fluid by using a flow of the fluid created by microfluidic structures. A biochip is formed by arranging such microfluidic structures on a chip-type platform so as to perform various assays, including biological reactions.

SUMMARY

According to an aspect of the present invention, a fluid controlling apparatus includes an inlet through which a fluid is introduced; a channel portion connected to the inlet; an outlet that is connected to the channel portion and through which the fluid is discharged; and at least one fluid resisting portion disposed between the inlet and the outlet.

The fluid resisting portion may be formed in the shape of a diamond, a triangle, a quadrangle, a circle, an oval, a fan shape, or a streamlined shape.

The fluid controlling apparatus may further include a first connecting portion that connects the inlet and the channel portion and is formed as a tapered structure, and a second connecting portion that connects the channel portion and the outlet and is formed as a tapered structure.

A ratio of a width W to a length L of the channel portion may range from about 3:1 to about 100:1.

According to another aspect of the present invention, a filter including the fluid controlling apparatus is provided. The filter includes an inlet through which a fluid including target materials is introduced; a channel portion connected to the inlet; a filter portion that is disposed within the channel portion and filters the target materials; an outlet that is connected to the channel portion and through which the fluid is discharged; and at least one fluid resisting portion disposed between the inlet and the outlet.

The at least one fluid resisting portion may be disposed in at least one of a space between the inlet and the filter portion and a space between the filter portion and the outlet.

The fluid resisting portion may be formed in the shape of a diamond, a triangle, a quadrangle, a circle, an oval, a fan shape, or a streamlined shape.

The filter may further include a first connecting portion that connects the inlet and the channel portion and is formed as a tapered structure, and a second connecting portion that connects the channel portion and the outlet and is formed as a tapered structure.

A ratio of a width W to a length L of the channel portion may range from about 3:1 to about 100:1.

The filter portion may include a plurality of filter units.

Each of the filter units may include a first portion having a plurality of protrusions protruding in a first direction, and a second portion that is spaced apart from the first portion to face the first portion and has a plurality of protrusions that protrude in a second direction, that is, toward the first portion, and correspond to the plurality of protrusions of the first portion.

Each of the filter units may further include a third portion disposed between the first and second portions, a first fluid discharge channel is formed between the first and third portions, and a second fluid discharge channel is formed between the second and third portions.

The filter portion may include a plurality of filter sequences including the filter units.

According to another aspect of the present invention, a bio-chip including the fluid controlling apparatus is provided. The biochip includes an inlet through which a fluid including target materials is introduced; a channel portion connected to the inlet; a reaction portion that is disposed within the channel portion and reacts to the target materials; an outlet that is connected to the channel portion and through which the fluid is discharged; and at least one fluid resisting portion disposed between the inlet and the outlet.

The at least one fluid resisting portion may be disposed in at least one of a space between the inlet and the reaction portion and a space between the reaction portion and the outlet.

The fluid resisting portion may be formed in the shape of a diamond, a triangle, a quadrangle, a circle, an oval, a fan shape, or a streamlined shape.

The bio-chip may further include a first connecting portion that connects the inlet and the channel portion and is formed as a tapered structure; and a second connecting portion that connects the channel portion and the outlet and is formed as a tapered structure.

A ratio of a width W to a length L of the channel portion may range from about 3:1 to about 100:1.

The reaction portion may include a plurality of biomolecules capable of reacting to the target materials.

The plurality of biomolecules may be arranged in a 2-dimensional array.

The plurality of biomolecules may include nucleic acids, sugar, or proteins.

BRIEF DESCRIPTION OF THE DRAWINGS

These and/or other aspects will become apparent and more readily appreciated from the following description of the embodiments, taken in conjunction with the accompanying drawings of which:

FIG. 3C is a schematic plan view of filter sequences in each of which a plurality of filter units are arranged, according to an embodiment of the present invention;

DETAILED DESCRIPTION

Figure 1A:
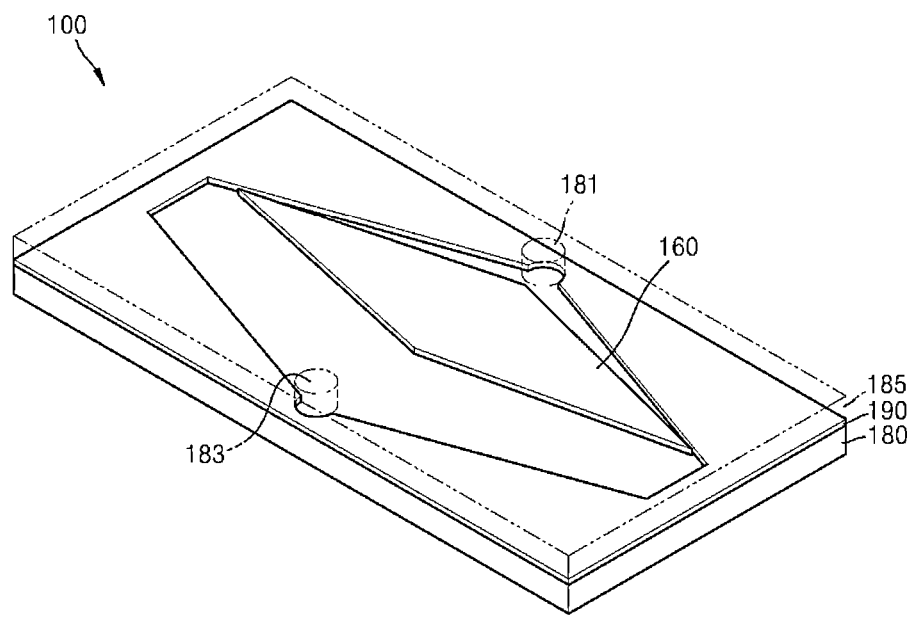
FIG. 1A is a schematic perspective view of a fluid controlling apparatus according to an embodiment of the present invention.

Various example embodiments will now be described more fully with reference to the accompanying drawings in which some example embodiments are shown.

Detailed illustrative example embodiments are disclosed herein. However, specific structural and functional details disclosed herein are merely representative for purposes of describing example embodiments. This invention may be embodied in many alternate forms and should not be construed as limited to only the example embodiments set forth herein. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element or layer is referred to as being "formed on" another element or layer, it can be directly or indirectly formed on the other element or layer. That is, for example, intervening elements or layers may be present. In contrast, when an element or layer is referred to as being "directly formed on" another element, there are no intervening elements or layers present. Other words used to describe the relationship between elements or layers should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

In the drawings, the thicknesses of layers and regions are exaggerated for clarity. Like reference numerals in the drawings denote like elements. Expressions such as "at least one of," when preceding a list of elements, modify the entire list of elements and do not modify the individual elements of the list.

Certain embodiments described herein refer to portions or materials that react to a target material. Reaction with a target material can be any reaction to or with a target material including, without limitation, interaction with a target material such as the binding of a target material (e.g., a nucleic acid, protein, cell, or other target material) by a probe or other capture agent.

Figure 1B:
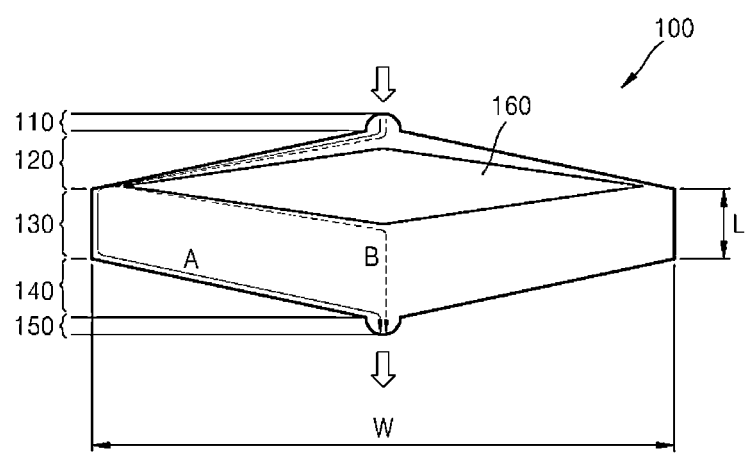
FIG. 1B is a schematic plan view of the fluid controlling apparatus shown in FIG. 1A.

FIG. 1A is a schematic perspective view of a fluid controlling apparatus 100 according to an embodiment of the present invention, and FIG. 1B is a schematic plan view of the fluid controlling apparatus 100.

Referring to FIGS. 1A and 1B, the fluid controlling apparatus 100 may include a first substrate 180, and a second substrate 190 disposed on the first substrate 180. The second substrate 190 may include an inlet 110 through which a fluid is introduced, a channel portion 130 connected to the inlet 110, an outlet 150 that is connected to the channel portion 130 and through which the fluid is discharged, and at least one fluid resisting portion 160 disposed between the inlet 110 and the outlet 150. The fluid controlling apparatus 100 may further include a third substrate 185 disposed on the second substrate 190, and the third substrate 185 may include a plurality of through holes (e.g., 181 and 183) formed therein.

At least one of the first and third substrates 180 and 185 may be transparent. When the first substrate 180 or the third substrate 185 is a transparent substrate, a fluid in the fluid controlling apparatus 100 may be easily observed. For example, the first and third substrates 180 and 185 may include glass, quartz, plastic, polymer, or the like. The third substrate 185 may include a first through hole 181 and a second through hole 183 respectively connected to the inlet 110 and the outlet 150. The first and second through holes 181 and 183 are depicted as perpendicular to the face of the substrate, but (when used) can be positioned anywhere on the substrate and with any orientation that allows a fluid to be introduced to the inlet and allowed to flow from the outlet.

The second substrate 190 may be disposed on the first substrate 180 and may include the inlet 110, the channel portion 130, the outlet 150, the fluid resisting portion 160, and the like. The inlet 110, the channel portion 130, the outlet 150, the fluid resisting portion 160, or the like may be formed by patterning the second substrate 190. The second substrate 190 may be formed of, for example, silicon, a silicon based polymer material, or a polymer material. In detail, the second substrate 190 may be formed of, for example, acrylate, polymethylacrylate, polymethylmethacrylate (PMMA), polycarbonate, polystyrene, polyimide, epoxy resin, polydimethylsiloxane (PDMS), parylene, or the like.

The inlet 110 is an entrance through which a fluid is introduced, and may be connected to the first through hole 181 formed in the third substrate 185 as shown in FIG. 1A. In other words, the fluid may be introduced into the inlet 110 via the first through hole 181. The fluid may be introduced into the inlet 110 via another path (not shown) connected to the second substrate 190 instead of via the first through hole 181.

The channel portion 130 may be connected to the inlet 110, and a first connecting portion 120 may be disposed between the channel portion 130 and the inlet 110. The first connecting portion 120 may be formed as a tapered structure and may be formed as a structure that widens in a direction from the inlet 110 to the channel portion 130.

A width W of the channel portion 130 may be greater than a length L thereof. For example, a ratio of the width W to the length L of the channel portion 130 may be about 3:1 or more than about 3:1. Further, the ratio of the width W to the length L of the channel portion 130 may range from about 3:1 to about 100:1. More particularly, the ratio of the width W to the length L of the channel portion 130 may range from about 3:1 to about 50:1 or from about 3:1 to about 30:1. If the width W of the channel portion 130 is greater than the length L thereof, a maximum speed of a fluid and a maximum pressure applied to the channel portion 130 may be reduced.

The dimensions of the channel portion will depend upon the application in which the fluid control apparatus is used. For instance, when used in a filter or biochip, as described herein, the channel portion should have dimensions suitable for the introduction and flow of the biological material to be introduced into the channel. By way of further illustration, the channel portion can have a width of about from 0.5 mm to 50 mm, for example, 30 mm, and a length of about from 1 mm to 100 mm, for example, 30 mm.

The at least one fluid resisting portion 160 may be disposed at any position between the inlet 110 and the outlet 150. As shown in FIG. 1B, the fluid resisting portion 160 may be disposed near the inlet 110; however, the fluid resisting portion 160 also may be disposed near the outlet 150. The fluid resisting portion 160 may be disposed across the first connecting portion 120 and the channel portion 130; or the fluid resisting portion 160 may be disposed within the channel portion 130 or near the outlet 150. Furthermore, a plurality of the fluid resisting portions 160 may be disposed between the inlet 110 and the outlet 150. The fluid resisting portion 160 may be shaped as a diamond as shown in FIG. 1B, but the present invention is not limited thereto. The fluid resisting portion 160 may be shaped as another polygon, such as a triangle or a quadrangle, or may be a circle, an oval, a fan shape, a streamlined shape (e.g., tear drop shape, the shape of an airfoil, or other streamlined shape), or a combination thereof. The fluid resisting portion or plurality of fluid resisting portions are appropriately sized so as to allow fluid, perhaps containing biological materials, to flow from the inlet around the fluid resisting portion and to the outlet.

The fluid resisting portion 160 may control a speed of a fluid introduced into the inlet 110, a distribution of stream lines of the fluid, and the like. For example, the fluid resisting portion 160 may reduce the speed of the fluid and keep the speed (velocity), fore example, 5 μm/ms, of the fluid in the channel portion 130 within a certain range, by resisting the fluid flowing in the channel portion 130. The fluid resisting portion 160 may allow stream lines to be evenly distributed in the channel portion 130 and lengths of the stream lines to be similar to one another. For example, a stream line A flowing along an edge, namely, a wall, of the channel portion 130 and a stream line B flowing along a center of the channel portion 130 have different paths, but lengths of the stream lines A and B may be similar to each other. In one aspect, the fluid resisting portion is configured (e.g., sized and positioned) such that the speed of the fluid is more evenly distributed across the channel portion as compared to the speed of the same fluid across the channel in the absence of the fluid resisting portion.

The outlet 150 is an exit that is connected to the channel portion 130 and through which a fluid is discharged. A second connecting portion 140 may be further disposed between the channel portion 130 and the outlet 150. The second connecting portion 140 may be formed as a tapered structure and may be formed as a structure that narrows in a direction from the channel portion 130 to the outlet 150. The outlet 150 may be connected to the second through hole 183 formed in the third substrate 185 as shown in FIG. 1A. In other words, the fluid may be discharged from the outlet 150 via the second through hole 183. The fluid may be discharged from the outlet 150 via another path (not shown) connected to the second substrate 190 instead of via the second through hole 183.

The fluid controlling apparatus 100 may include the fluid resisting portion 160 between the inlet 110 and the outlet 150 to control a speed of a fluid, a distribution of stream lines of the fluid, and the like. In other words, the fluid control apparatus 100 may reduce the speed of the fluid flowing in the channel portion 130 or keep the speed of the fluid in the channel portion 130 within a certain range. The fluid control apparatus 100 may also keep a density of the stream lines of the fluid in the channel portion 130 within a certain range.

Figure 2A:
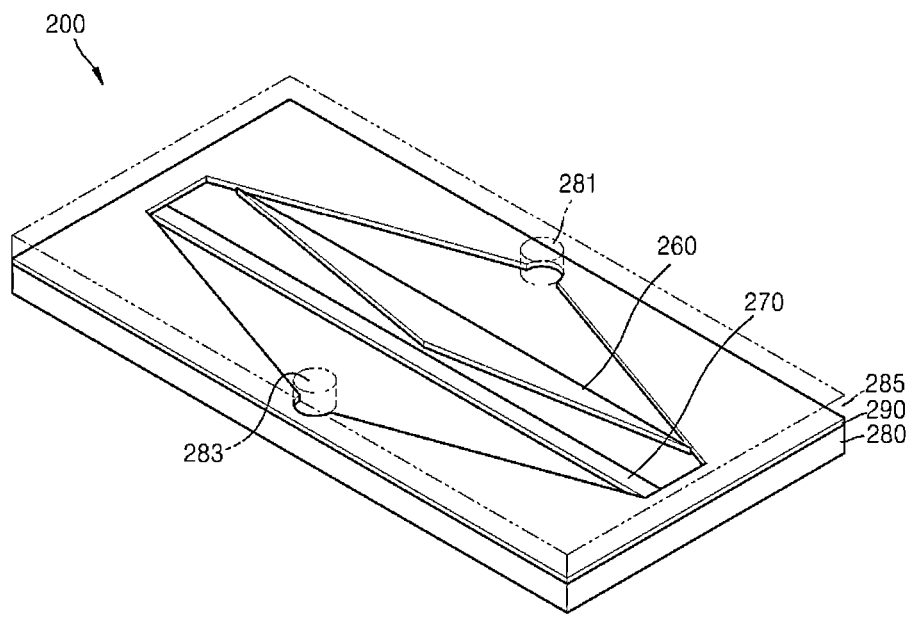
FIG. 2A is a schematic perspective view of a filter according to an embodiment of the present invention.
Figure 2B:
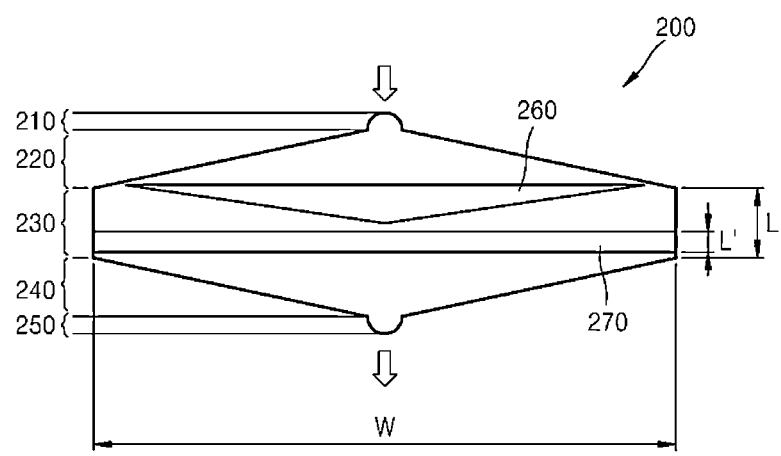
FIG. 2B is a schematic plan view of the filter shown in FIG. 2A.

FIG. 2A is a schematic perspective view of a filter 200 according to an embodiment of the present invention. FIG. 2B is a schematic plan view of the filter 200 shown in FIG. 2A.

Referring to FIGS. 2A and 2B, the filter 200 may include a first substrate 280, and a second substrate 290 disposed on the first substrate 280. The second substrate 290 may include an inlet 210 through which a fluid including target materials is introduced, a channel portion 230 connected to the inlet 210, a filter portion 270 that filters the target materials and is disposed within the channel portion 230, an outlet 250 that is connected to the channel portion 230 and through which the fluid is discharged, and at least one fluid resisting portion 260 disposed between the inlet 210 and the outlet 250. The filter 200 may further include a third substrate 285 disposed on the second substrate 290, and the third substrate 285 may include a plurality of through holes formed therein.

At least one of the first and third substrates 280 and 285 may be transparent. When the first substrate 280 or the third substrate 285 is a transparent substrate, a fluid or target materials in the fluid in the filter 200 may be easily observed. For example, the first and third substrates 280 and 285 may include glass, quartz, plastic, polymer, or the like. The third substrate 285 may include a first through hole 281 and a second through hole 283 respectively connected to the inlet 210 and the outlet 250.

The second substrate 290 may be disposed on the first substrate 280 and may include the inlet 210, the channel portion 230, the filter portion 270, the outlet 250, the fluid resisting portion 260, and the like. The inlet 210, the channel portion 230, the filter portion 270, the outlet 250, the fluid resisting portion 260, or the like may be formed by patterning the second substrate 290. The second substrate 290 may be formed of, for example, silicon, a silicon based polymer material, or a polymer material. In detail, the second substrate 290 may be formed of, for example, acrylate, polymethylacrylate, polymethylmethacrylate (PMMA), polycarbonate, polystyrene, polyimide, epoxy resin, polydimethylsiloxane (PDMS), parylene, or the like.

The inlet 210 is an entrance through which a fluid including target materials is introduced, and may be connected to the first through hole 281 formed in the third substrate 285 as shown in FIG. 2A. In other words, the fluid may be introduced into the inlet 210 via the first through hole 281. The fluid may be introduced into the inlet 210 via another path (not shown) connected to the second substrate 290 instead of via the first through hole 281.

Target materials to be captured by the filter 200 may be various biological materials. Biological materials may include cells or biological molecules. Cells may include various cells such as cancer cells, red blood cells (RBCs), white blood cells (WBCs), phagocytes, animal cells, or plant cells. Also, biological molecules may include various biomolecules constituting a living organism, such as proteins, lipids, or nucleic acid including deoxyribonucleic acid (DNA) or ribonucleic acid (RNA). However the present embodiment is not limited thereto.

Biological molecules may include aptamers, antigens, antibodies, enzymes, enzyme substrates, enzyme inhibitors, receptors, receptor ligands, or the like. If target materials are biological molecules, since sizes of biological molecules range from several nanometers (nm) to several hundred nm, a size of a filter unit (not shown) included in the filter 200, that is, a size of a capturing portion of the filter unit, may range from several nm to several hundred nm.

For example, target materials may include circulating tumor cells (CTCs) included in blood. The number of CTCs may be so small that only one CTC is detected from among about $10^9$ cells. For example, in the case of breast cancer, about 5 CTCs or less may be detected in about 7.5 milliliters (ml) of blood, and in the case of colon cancer, 3 CTCs or less may be detected in about 7.5 ml of blood. Accordingly, it needs to capture such a small number of CTCs without loss. Also, since CTCs are easily destructed, external environmental factors that may destruct CTCs need to be minimized.

The channel portion 230 may be connected to the inlet 210, and a first connecting portion 220 may be disposed between the channel portion 230 and the inlet 210. The first connecting portion 220 may be formed as a tapered structure and may be formed as a structure that widens in a direction from the inlet 210 to the channel portion 230. A width W of the channel portion 230 may be greater than a length L thereof. For example, a ratio of the width W to the length L of the channel portion 230 may be more than about 3:1. Further, the ratio of the width W to the length L of the channel portion 230 may range from about 3:1 to about 100:1. More particularly, the ratio of the width W to the length L of the channel portion 230 may range from about 3:1 to about 50:1 and from about 3:1 to about 30:1. If the width W of the channel portion 230 is greater than the length L thereof, a maximum speed of a fluid and a maximum pressure applied to the channel portion 230 may be reduced.

The filter portion 270 may be disposed within the channel portion 230 and may capture target materials from a fluid. The filter portion 270 may be disposed between the fluid resisting portion 260 and the outlet 250 or between the inlet 210 and the fluid resisting portion 260. A plurality of filter portions 270 can be used, wherein the filter portions are positioned between the fluid resisting portion 260 and the outlet 250, between the inlet 210 and the fluid resisting portion 260, or both. A width W of the filter portion 270 may be greater than a length L' thereof. For example, a ratio of the width W to the length L' of the filter portion 270 may be more than about 3:1. Further, the ratio of the width W to the length L' of the filter portion 270 may range from about 3:1 to about 100:1. More particularly, the ratio of the width W to the length L' of the filter portion 270 may range from about 3:1 to about 50:1 and from about 3:1 to about 30:1. Each filter portion 270 may include a plurality of filter units (not shown), and more particularly, a plurality of filter sequences (not shown) obtained by aligning the plurality of filter units (not shown) with one another. The filter units and the filter sequences will be described later.

The at least one fluid resisting portion 260 may be disposed between the inlet 210 and the outlet 250. As shown in FIG. 2B, the fluid resisting portion 260 may be disposed near the inlet 210. The at least one fluid resisting portion 260 may be disposed between the inlet 210 and the filter portion 270. The fluid resisting portion 260 may be disposed within the channel portion 230 or near the outlet 250. A plurality of the fluid resisting portions 260 may be disposed between the inlet 210 and the outlet 250, in which case the fluid resisting portions can be disposed between the inlet 210 and the filter portion 270, between the filter portion 270 and the outlet 250, or both. Also, each filter portion 270 may be disposed between the plurality of fluid resisting portions 260.

The fluid resisting portion 260 may be shaped as a triangle or an inverted triangle as shown in FIG. 2B, and the present invention is not limited thereto. The fluid resisting portion 160 may be shaped as another polygon, such as a diamond or a quadrangle, or may be a circle, an oval, a fan shape, a streamlined shape, or a combination thereof. The fluid resisting portion 260 may control a speed of a fluid introduced into the inlet 210, a distribution of stream lines of the fluid, and the like. For example, the fluid resisting portion 260 may reduce the speed of the fluid and keep the speed of the fluid in the filter portion 270 within a certain range, by resisting the fluid flowing in the channel portion 230, and more particularly, in the filter portion 270. The fluid resisting portion 260 may allow the stream lines to be evenly distributed in the channel portion 230, and more particularly, in the filter portion 270, and lengths of the stream lines to be similar to one another.

The outlet 250 is an exit that is connected to the channel portion 230 and through which a residual fluid from which target materials have been filtered out is discharged. A second connecting portion 240 may be further disposed between the channel portion 230 and the outlet 250. The second connecting portion 240 may be formed as a tapered structure and may be formed as a structure that narrows in a direction from the channel portion 230 to the outlet 250. The outlet 250 may be connected to the second through hole 283 formed in the third substrate 285 as shown in FIG. 2A. In other words, the fluid may be discharged from the outlet 250 via the second through hole 283. The fluid may be discharged from the outlet 250 via another path (not shown) connected to the second substrate 290 instead of via the second through hole 283.

The filter 200 may include the fluid resisting portion 260 between the inlet 210 and the outlet 250 to control a speed of a fluid, a distribution of stream lines of the fluid, and the like. In other words, the filter 200 may reduce the speed of the fluid flowing in the channel portion 230, and more particularly, in the filter portion 270, or keep the speed of the fluid in the filter portion 270 within a certain range. The filter 200 may also keep a density of the stream lines of the fluid in the filter portion 270 within a certain range. Accordingly, a collection rate of the filter 200 at which target materials are captured and purity of target materials may be improved.

Other aspects of the filter are as discussed with respect to the fluid control apparatus.

Figure 3A:
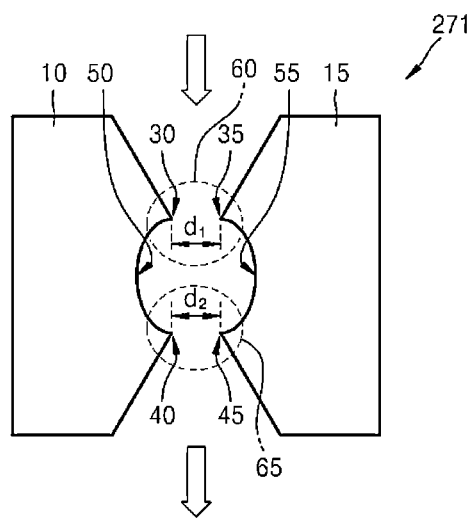
FIGS. 3A and 3B are schematic plan views of filter units included in a filter portion of a filter according to an embodiment of the present invention.
Figure 3B:
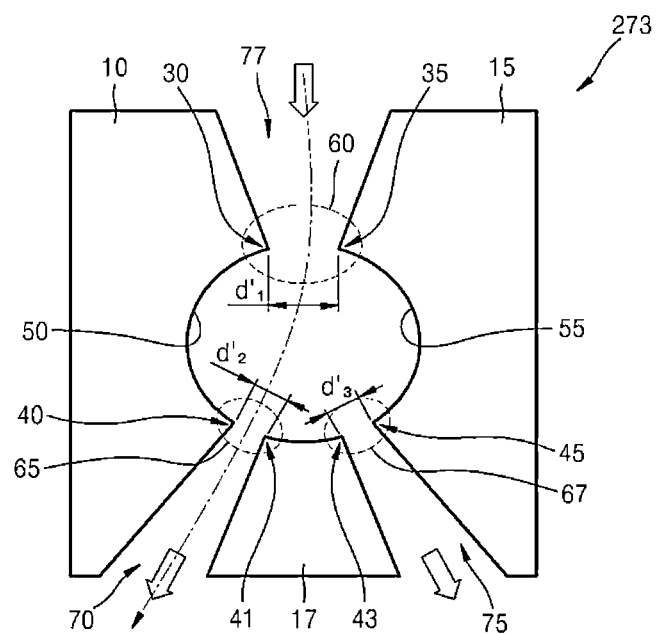

FIGS. 3A and 3B are plan views of filter units 271 and 273 included in the filter portion 270 of the filter 200, according to an embodiment of the present invention. FIG. 3C is a schematic plan view of filter sequences 275 in each of which a plurality of filter units are arranged, according to an embodiment of the present invention.

Referring to FIG. 3A, the filter unit 271 may include a first portion 10, and a second portion 15 that is spaced apart from the first portion 10 to face the first portion 10. The first portion 10 may include a plurality of protrusions, for example, first and second protrusions 30 and 40, protruding in a first direction, and the first direction may be a direction in which the first portion 10 faces the second portion 15. The second portion 15 may include a plurality of protrusions, for example, third and fourth protrusions 35 and 45, protruding in a second direction, that is, toward the first portion 10. The third and fourth protrusions 35 and 45 of the second portion 15 may be disposed to correspond to the first and second protrusions 30 and 40 of the first portion 10, respectively.

The plurality of protrusions of the first portion 10 may include the first protrusion 30 and the second protrusion 40, which are spaced apart from each other. The plurality of protrusions of the second portion 15 may include the third protrusion 35 and the fourth protrusion 45, which are spaced apart from each other. Here, the first protrusion 30 and the third protrusion 35 may be spaced apart from each other to face each other, and a first distance d1 between the first protrusion 30 and the third protrusion 35 may be adjusted according to sizes of target molecules to be filtered. The first distance d1 between the first protrusion 30 and the third protrusion 35 may range from several micrometers ($\mu$m) to several hundred $\mu$m. For example, the first distance d1 may range from about 1 $\mu$m to about 500 $\mu$m, and particularly, the first distance d1 may range from about 5 $\mu$m to about 100 $\mu$m.

The second protrusion 40 and the fourth protrusion 45 may also be spaced apart from each other to face each other. A second distance d2 between the second protrusion 40 and the fourth protrusion 45 may be adjusted according to sizes of target molecules to be captured. The second distance d2 between the second protrusion 40 and the fourth protrusion 45 may range from several $\mu$m to several hundred $\mu$m. For example, the second distance d2 may range from about 1 $\mu$m to about 500 $\mu$m, and particularly, the second distance d2 may range from about 5 $\mu$m to about 100 $\mu$m. The first distance d1 between the first protrusion 30 and the third protrusion 35 may be greater than or equal to the second distance d2 between the second protrusion 40 and the fourth protrusion 45. A size of the filter unit 271 may refer to the first distance d1 between the first protrusion 30 and the third protrusion 35 or the second distance d2 between the second protrusion 40 and the fourth protrusion 45.

The filter unit 271 may include a first capturing portion 60 and a second capturing portion 65. A fluid including target molecules may be introduced in a direction indicated by an arrow on an upper side of FIG. 3A, and may be discharged in a direction indicated by an arrow on a lower side of FIG. 3A. The target molecules may be captured by at least one of the first capturing portion 60 and the second capturing portion 65. Accordingly, since the filter unit 271 includes more structures capable of capturing target molecules than a comparative filter having one capturing structure, the target molecules are more likely to be captured in the filter unit 271 than in the comparative filter.

The first capturing portion 60 may be formed by the first protrusion 30 and the third protrusion 35, and may capture target molecules. The first protrusion 30 and the third protrusion 35 may be tapered toward ends thereof, so that the target molecules may be easily filtered by the first capturing portion 60. That is, the target molecules included in a fluid may be supported by the first capturing portion 60 so as not to leak out of the filter unit 271 along with the fluid. Also, although the ends of the first protrusion 30 and the third protrusion 35 are sharp, the present embodiment is not limited thereto. That is, the ends of the first protrusion 30 and the third protrusion 35 may be blunt. In this case, while the target molecules pass between the blunt ends of the first protrusion 30 and the third protrusion 35, a speed of the target molecules may be reduced due to a friction force.

The second capturing portion 65 may be formed by the second protrusion 40 and the fourth protrusion 45, and may also capture target molecules. The second protrusion 40 and the fourth protrusion 45 may be tapered toward ends thereof, so that the target molecules may be easily filtered by the second capturing portion 65. That is, the target molecules included in a fluid may be supported by the second capturing portion 65 so as not to leak out of the filter unit 271 along with the fluid. Also, the ends of the second protrusion 40 and the fourth protrusion 45 may be sharp. A space between the first protrusion 30 and the second protrusion 40 and a space between the third protrusion 35 and the fourth protrusion 45 may be defined by curved surfaces 50 and 55, and thus spaces where captured materials exist are increased, and damage to target molecules to be captured due to contact with the filter unit 271 may be reduced or effectively prevented.

When the second capturing portion 65 captures target molecules, even when a fluid leaking out of the filter unit 271 flows backward through the filter unit 271, the first protrusion 30 and the third protrusion 35 may support the captured target molecules. Accordingly, leaking out of the captured target molecules from the filter unit 271 along with the fluid is reduced or effectively prevented. Also, if the second distance d2 between the second protrusion 40 and the fourth protrusion 45 is less than the first distance d1 between the first protrusion 30 and the third protrusion 35, the target molecules are more likely to be captured. Also, different sizes of the target molecules may be captured by the first and second capturing portions 60 and 65. The first capturing portion 60 formed by the first protrusion 30 and the third protrusion 35 and the second capturing portion 65 formed by the second protrusion 40 and the fourth protrusion 45 may be referred to as obstacle structures. Accordingly, the filter unit 271 may include multiple obstacle structures.

For example, since the filter unit 271 may capture CTCs respectively in the first capturing portion 60 and the second capturing portion 65, target molecules are more likely to be captured. That is, since CTCs are surrounded by flexible cell membranes, the CTCs may be deformed to some extent. Undeformed CTCs may be captured by the first capturing portion 60, and deformed CTCs may be captured by the second capturing portion 65, thereby reducing the number of CTCs that are not filtered, that is, CTCs that are lost. Since the filter unit 271 may filter only the desired target molecules, a time taken to analyze the target molecules may be reduced. Also, since there is no need to re-separate the desired target molecules from other molecules, efficiency and convenience may be improved.

Referring to FIG. 3B, the filter unit 273 may include a first portion 10, a second portion 15 that is spaced apart from the first portion 10 to face the first portion 10, and a third portion 17 disposed between the first and second portions 10 and 15. An introduction channel 77 may be disposed between upper portions of the first and second portions 10 and 15. The third portion 17 may be disposed between lower portions of the first and second portions 10 and 15. A first discharge channel 70 may be formed between the first and third portions 10 and 17, and a second discharge channel 75 may be formed between the second and third portions 15 and 17. More discharge channels may be formed in the filter unit 273 by dividing the filer unit 273 into more portions.

The first portion 10 may include a first protrusion 30 and a second protrusion 40, protruding in a first direction, and the first direction may be a direction in which the first portion 10 faces the second portion 15. The second portion 15 may include a third protrusion 35 and a fourth protrusion 45, protruding in a second direction, that is, toward the first portion 10. The third portion 17 may include a fifth protrusion 41 protruding in the second direction, that is, toward the first portion 10, and a sixth protrusion 43 protruding in the first direction, that is, toward the second portion 15.

The first protrusion 30 may correspond to the third protrusion 35, and a first capturing portion 60 may be formed by the first protrusion 30 and the third protrusion 35. The second protrusion 40 may correspond to the fifth protrusion 41, and a second capturing portion 65 may be formed by the second protrusion 40 and the fifth protrusion 41. The fourth protrusion 45 may correspond to the sixth protrusion 43, and a third capturing portion 67 may be formed by the fourth protrusion 45 and the sixth protrusion 43.

A size of the first capturing portion 60, that is, a distance d1 between the first and third protrusions 30 and 35, a size of the second capturing portion 65, that is, a distance d2 between the second and fifth protrusions 40 and 41, or a size of the third capturing portion 67, that is, a distance d3 between the fourth and sixth protrusions 45 and 43 may be adjusted according to sizes of target materials to be filtered. The distances d1, d2, and d3 may range from several μm to several hundred μm. For example, the distances d1, d2, and d3 may range from about 1 μm to about 500 μm, and particularly, range from about 5 μm to about 100 μm.

Since the filter unit 273 may include a plurality of capturing portions, for example, the first capturing portion 60, the second capturing portion 65, and the third capturing portion 67, target molecules are more likely to be captured in the filter unit 273. A fluid including the target molecules may be introduced in a direction indicated by an arrow of FIG. 3B, and may be discharged via the first discharge channel 70 or the second discharge channel 75 shown in a lower side of FIG. 3B. More generally, the first discharge channel 70 connected to the second capturing portion 65 or the second discharge channel 75 connected to the third capturing portion 67 may serve as a discharge path of the fluid. For example, when the third capturing portion 67 captures a target material, although the target material blocks the second discharge channel 75, the fluid may be discharged to the first discharge channel 70 connected to the second capturing portion 65 having not yet captured the target material. Further, molecules other than the target material, along with the fluid, may be discharged to the first discharge channel 70. Thus, a pressure inside the filter unit 273 is kept low, and thus application of a high pressure to the target material and losing of the target material from the filter unit 273 may be reduced or effectively prevented.

Referring to FIG. 3C, the filter portion 270 of the filter 200 may include a plurality of filter sequences 275 arranged in parallel to each other in a direction from an inlet to an outlet. Each filter sequence 275 may include a plurality of the filter units 273. The plurality of filter units 273 may be spaced apart from each other or be adjoined with each other and be aligned with each other. Alternatively, each filter sequence 275 may include a plurality of the filter units 271.

The plurality of filter sequences 275 may include an nth (n is a natural number) filter sequence 277 and an (n+1)th filter sequence 279 arranged in parallel to each other in the direction from the inlet to the outlet. A filter unit 273 included in the nth filter sequence 277 and a filter unit 273 included in the (n+1)th filter sequence 279 may not be disposed with sides thereof aligned. That is, filter units included in the nth filter sequence 277 and filter units included in the (n+1)th filter sequence 279 may be disposed in a zigzag manner. Thus, if the nth filter sequence 277 and the (n+1)th filter sequence 279 are disposed in a zigzag manner, a fluid, target molecules included in the fluid, and other molecules may have various movement paths. Alternatively, the filter units included in the nth filter sequence 277 and the filter units included in the (n+1)th filter sequence 279 may not be disposed in a zigzag manner and may be disposed with their sides aligned.

First, second, and third convex portions 80, 81, and 83 may be further disposed on front surfaces of the nth and (n+1)th filter sequences 277 and 279 through which a fluid is introduced and on rear surfaces thereof through which the fluid is discharged. The first, second, and third convex portions 80, 81, and 83 may protrude from the front surfaces and the rear surfaces and be referred to as stagnation prevention portions that prevent stagnation of the fluid. The first convex portion 80 may be disposed between introduction channels 77 of adjacent filter units. The second convex portion 81 may be disposed between first and second discharge channels 70 and 75. The third convex portion 83 may be disposed between a second discharge channel 75 and a first discharge channel 70 of adjacent filter units 273. The first, second, and third convex portions 80, 81, and 83 may reduce or effectively prevent accumulation of target materials or other molecules due to a stagnant fluid around the nth filter sequence 277 and the (n+1)th filter sequence 279.

Figure 4A:
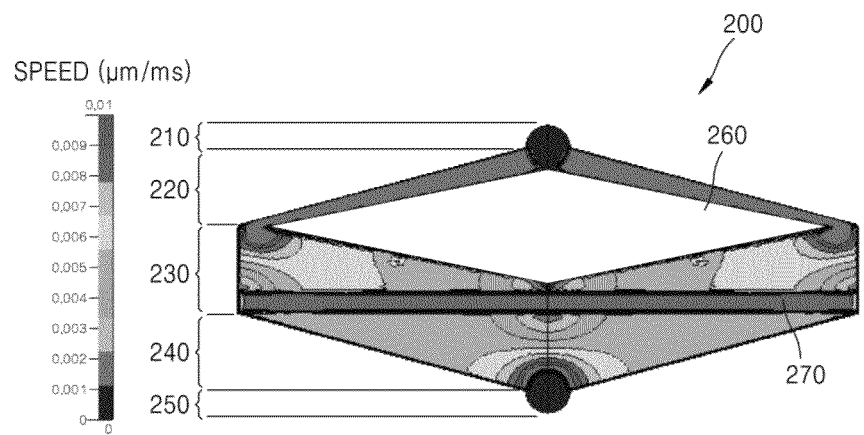
FIG. 4A illustrates a distribution of speeds of a fluid in the filter shown in FIGS. 2A and 2B.
Figure 4B:
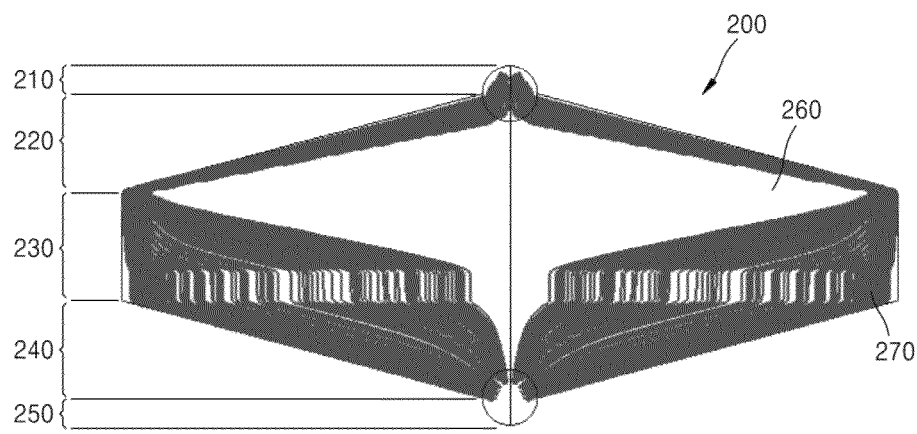
FIG. 4B illustrates stream lines in the filter shown in FIGS. 2A and 2B.

FIG. 4A illustrates a distribution of speeds of a fluid in the filter 200 shown in FIGS. 2A and 2B, and FIG. 4B illustrates stream lines of the fluid in the filter 200 shown in FIGS. 2A and 2B.

Referring to FIG. 4A, a speed of a fluid in the filter portion 270 of the filter 200, namely, a mean flow speed, is kept almost constant. In certain embodiments, no more than about 10% (e.g., no more than about 8%, no more than about 5%, or no more than about 3% of the area of the filter portion exhibits a fluid flow that deviates more than ±5% from the mean flow speed. Results of measuring the flow speed in the filter portion 270 indicate that only about 2% or less of regions (flat, dimensional area) of the filter portion 270 have a flow speed that deviates more than ±5% from the mean flow speed in the filter portion 270.

Referring to FIG. 4B, stream lines in the filter 200 are evenly distributed. In particular, a density of the stream lines of a fluid flowing in the filter portion 270 is almost constant. A length of a stream line in a center portion of the filter 200 is similar to that of a stream line in an edge portion of the filter 200. Accordingly, in the filter 200, a speed of the fluid flowing in the filter portion 270 is nearly constant, and the density of the stream lines of the fluid is almost constant. Thus, a collection rate at which target materials are captured by the filter 200 and purity of target materials may be improved.

Figure 5A:
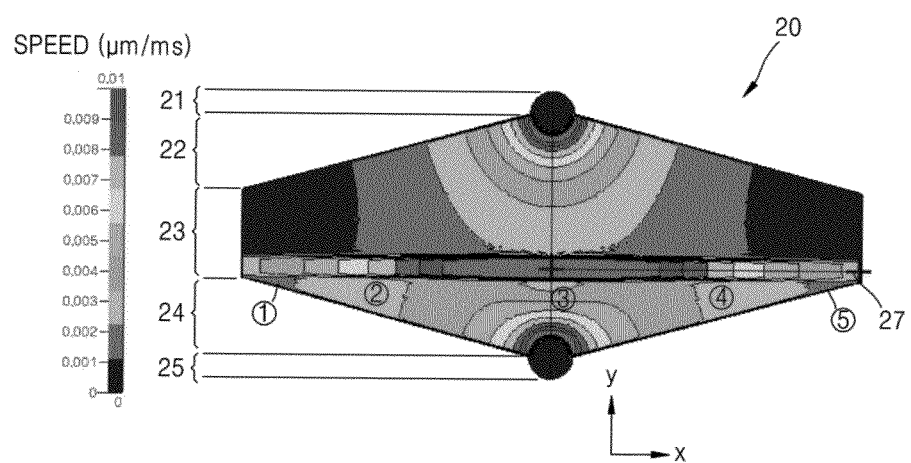
FIG. 5A illustrates a distribution of speeds of a fluid in a filter according to a comparative example.
Figure 5B:
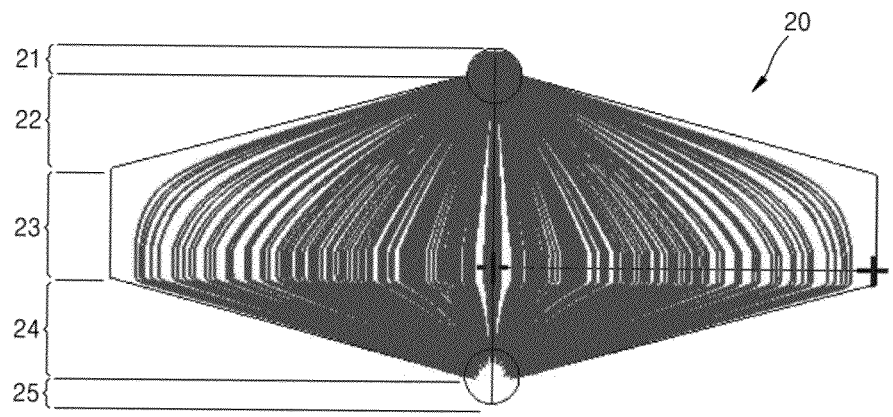
FIG. 5B illustrates stream lines in the filter according to the comparative example.

FIG. 5A illustrates a distribution of speeds of a fluid in a filter 20 according to a comparative example, and FIG. 5B illustrates stream lines of the fluid in the filter 20.

Referring to FIG. 5A, the filter 20 may include an inlet 21 through which a fluid is introduced, a channel portion 23 connected to the inlet 21, an outlet 25 that is connected to the channel portion 23 and through which the fluid is discharged, and a filter portion 27 disposed in the channel portion 23.

In the filter 20 according to a comparative example, a speed of a fluid in the filter portion 27 has a large deviation between a center portion and an edge portion of the filter portion 27. In other words, since the flow speed in the center portion of the filter portion 27 is high, a probability that target materials are lost from a filter unit may increase even though the target materials are captured. Since the flow speed in the edge portion of the filter portion 27 is low, the fluid stagnates and thus the target materials may not be captured. Results of measuring the flow speed in the filter portion 27 indicate that 94% of regions of the filter portion 27 have a flow speed that deviates more than ±5% from a mean flow speed.

Referring to FIG. 5B, stream lines in the filter 20 according to a comparative example are not evenly distributed, that is, are concentrated on a center portion of the filter 20. In other words, the stream lines are concentrated on the center portion of the filter portion 27 and are seldom distributed on the edge portion thereof. The stream lines in the center portion of the filter portion 27 are short, and those in the edge portion thereof are long.

Figure 6:
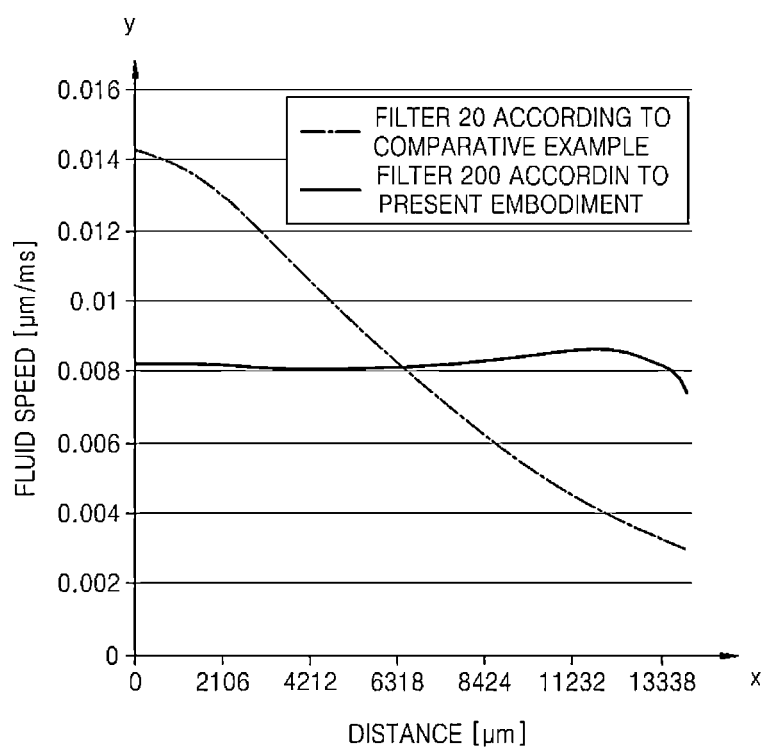
FIG. 6 is a graph showing flow speeds in a filter portion of the filter according to the embodiment of the present invention shown in FIGS. 2A and 2B and flow speeds in a filter portion of the filter according to the comparative example of FIGS. 5A and 5B.

FIG. 6 is a graph showing flow speeds in the filter portion 270 of the filter 200 according to the embodiment shown in FIGS. 2A and 2B and flow speeds in the filter portion 27 of the filter 20 according to the comparative example of FIGS. 5A and 5B. A speed of a fluid was measured from the center portions of the filter portions 270 and 27 to the edge portions thereof. In other words, the axis x indicates distances from the center portions of the filter portions 270 and 27, and the axis y indicates a speed of a fluid.

Referring to FIG. 6, in the filter 200 according to the present embodiment, speeds of a fluid measured from the center portion of the filter portion 270 to the edge portion of the filter portion 270 were kept almost constant. On the other hand, in the filter 20 according to a comparative example, speeds of a fluid measured from the center portion of the filter portion 27 to the edge portion of the filter portion 27 varied greatly. The flow speed at the center portion of the filter portion 27 was highest, and the flow speed sharply decreased from the center portion of the filter portion 27 to the edge portion of the filter portion 27.

Figure 7:
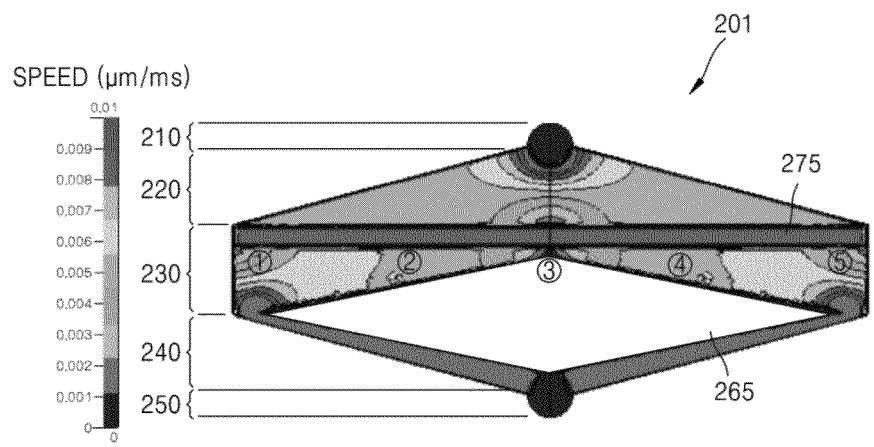
FIG. 7 is a schematic plan view of a filter according to another embodiment of the present invention.

FIG. 7 is a schematic plan view of a filter 201 according to another embodiment of the present invention.

Referring to FIG. 7, the filter 201 may include an inlet 210 through which a fluid including target materials is introduced, a channel portion 230 connected to the inlet 210, a filter portion 275 that is disposed in the channel portion 230 and filters the target materials, an outlet 250 that is connected to the channel portion 230 and through which the fluid is discharged, and at least one fluid resisting portion 265 disposed between the inlet 210 and the outlet 250. In the filter 201, the fluid resisting portion 265 may be disposed near the outlet 250, and the filter portion 275 may be disposed between the inlet 210 and the fluid resisting portion 265.

A speed of a fluid in the filter portion 275 of the filter 201, namely, a mean flow speed, is kept almost constant. Results of measuring the flow speed in the filter portion 275 indicate that only 2% of regions of the filter portion 275 have a flow speed that deviates more than ±5% from the mean flow speed. Since the filter 201 includes the filter portion 275 disposed in front of the fluid resisting portion 265, target materials or other materials may be stacked by the fluid resisting portion 265 or may be prevented from coagulating.

Figure 8:
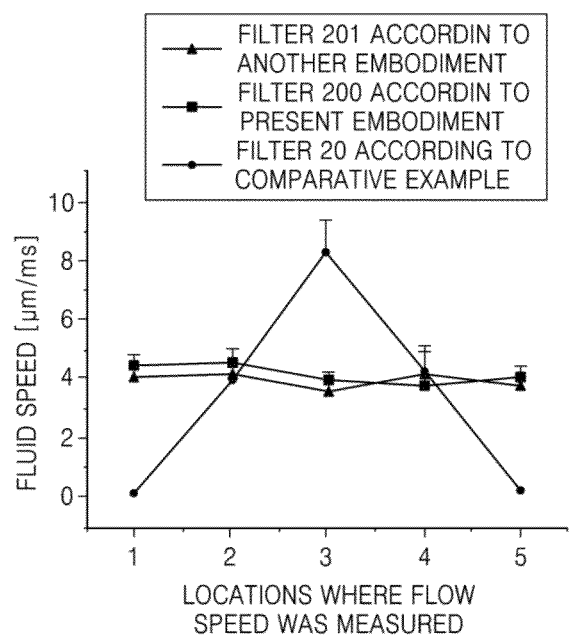
FIG. 8 is a graph showing flow speeds in filter portions of the filters according to the embodiments of the present invention shown in FIGS. 2A and 2B and FIG. 7 and flow speeds in a filter portion of the filter according to the comparative example of FIGS. 5A and 5B.

FIG. 8 is a graph showing flow speeds in the filter portions 270 and 275 of the filters 200 and 201 according to the embodiments shown in FIGS. 2A and 2B and FIG. 7 and flow speeds in the filter portion 27 of the filter 20 according to the comparative example of FIGS. 5A and 5B. The flow speeds were measured at first through fifth positions ① through ⑤ of each of the filter portions 270, 275, and 27 shown in FIGS. 4A, 5A, and 7.

Referring to FIG. 8, flow speeds in the filter portions 270 and 275 of the filters 200 and 201 according to the embodiments of the present invention were kept almost constant regardless of locations on the filter portions 270 and 275. According to this fact, a fluid resisting portion may be disposed in front of or at rear of the filter portions 270 and 275. On the other hand, in the filter 20 according to a comparative example, a flow speed in the center portion of the filter portion 27 was highest, and a flow speed greatly decreased toward both edge portions thereof.

Figure 9:
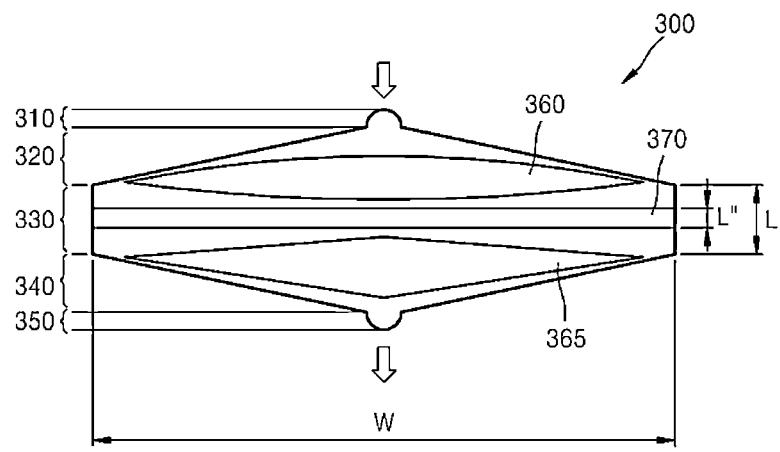
FIG. 9 is a schematic plan view of a bio-chip according to an embodiment of the present invention.

FIG. 9 is a schematic plan view of a bio-chip 300 according to an embodiment of the present invention.

Referring to FIG. 9, the bio-chip 300 may include an inlet 310 through which a fluid including target materials is introduced, a channel portion 330 connected to the inlet 310, a reaction portion 370 that is disposed within the channel portion 330 and reacts to the target materials, an outlet 350 that is connected to the channel portion 330 and through which the fluid is discharged, and at least one fluid resisting portion, namely, first and second fluid resisting portions 360 and 365, disposed between the inlet 310 and the outlet 350.

The channel portion 330 may be connected to the inlet 310, and a first connecting portion 320 may be disposed between the channel portion 330 and the inlet 310. The first connecting portion 320 may be formed as a tapered structure and may be formed as a structure that widens in a direction from the inlet 310 to the channel portion 330. A width W of the channel portion 330 may be greater than a length L thereof. For example, a ratio of the width W to the length L of the channel portion 330 may be more than about 3:1. Further, the ratio of the width W to the length L of the channel portion 330 may range from about 3:1 to about 100:1. More particularly, the ratio of the width W to the length L of the channel portion 330 may range from about 3:1 to about 50:1 and from about 3:1 to about 30:1. If the width W of the channel portion 330 is greater than the length L thereof, a maximum speed of a fluid or a maximum pressure applied to the channel portion 330 may be reduced.

The first and second fluid resisting portions 360 and 365 may be disposed between the inlet 310 and the outlet 350. Referring to FIG. 9, the first fluid resisting portion 360 may be disposed near the inlet 310, and the second fluid resisting portion 365 may be disposed near the outlet 350. The reaction portion 370 may be disposed between the first and second fluid resisting portions 360 and 365.

The first fluid resisting portion 360 may be shaped as a streamlined shape as shown in FIG. 9, and the second fluid resisting portion 365 may be shaped as a quadrangle instead of a diamond. However, the shapes of the first and second fluid resisting portions 360 and 365 are not limited thereto, and the shapes of the first and second fluid resisting portions 360 and 365 may be other polygons, such as diamonds or triangles, or may be a circle, an oval, a fan shape, a streamlined shape, or a combination thereof.

The first and second fluid resisting portions 360 and 365 may control speeds of a fluid introduced into the inlet 310, a distribution of stream lines of the fluid, and the like. For example, the first and second fluid resisting portions 360 and 365 may reduce the speeds of the fluid and keep the speed of the fluid in the reaction portion 370 within a certain range. This is accomplished by resisting the fluid flowing in the channel portion 330, and more particularly, in the reaction portion 370. The first and second fluid resisting portions 360 and 365 may allow the stream lines to be evenly distributed in the channel portion 330, and more particularly, in the reaction portion 370. Additionally, lengths of the stream lines may be similar to one another.

The reaction portion 370 may be disposed within the channel portion 330 and may biologically or chemically react to target materials included in a fluid. The reaction portion 370 may be disposed between the first and second fluid resisting portions 360 and 365. The reaction portion 370 may include a plurality of biomolecules capable of reacting to the target materials, and the plurality of biomolecules may be arranged in a 2-dimensional array in the reaction portion 370. The plurality of biomolecules may include nucleic acids (e.g., DNAs, RNAs, or aptamers), sugars or sugar binding moieties, polypeptides or proteins (e.g., antigensenzymes, receptors, receptor ligands, or antibodies), or the like.

The outlet 350 is an exit that is connected to the channel portion 330 and through which a fluid from which target materials have been filtered out is discharged. A second connecting portion 340 may be further disposed between the channel portion 330 and the outlet 350. The second connecting portion 340 may be formed as a tapered structure and may be formed as a structure that narrows in a direction from the channel portion 330 to the outlet 350.

The bio-chip 300 may include the first and second fluid resisting portions 360 and 365 between the inlet 310 and the outlet 350 to control a speed of a fluid, a distribution of stream lines of the fluid, and the like. In other words, the bio-chip 300 may reduce the speed of the fluid flowing in the channel portion 330, and more particularly, in the reaction portion 370, or keep the speed of the fluid in the reaction portion 370 within a certain range. The bio-chip 300 may also keep a density of the stream lines of the fluid in the reaction portion 370 within a certain range. Accordingly, the bio-chip 300 may cause a uniform reaction on the entire region of the reaction portion 370 and may increase reaction efficiency and reaction reproducibility.

Figure 10A:
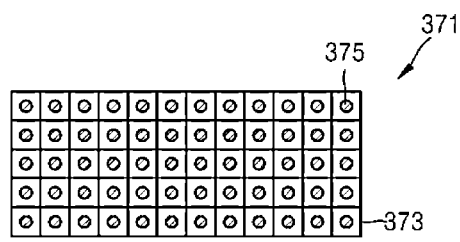
FIG. 10A is a schematic plan view of a reaction portion included in a bio-chip according to an embodiment of the present invention.
Figure 10B:
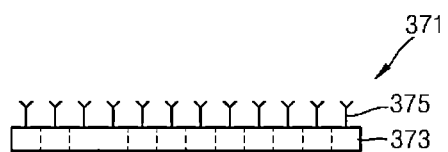
FIG. 10B is a schematic cross-sectional view of the reaction portion.

FIG. 10A is a schematic plan view of a reaction portion 371 included in a bio-chip according to an embodiment of the present invention, and FIG. 10B is a schematic cross-sectional view of the reaction portion 371.

Referring to FIGS. 10A and 10B, the reaction portion 371 may include a substrate 373 and a plurality of biomolecules 375 that are disposed on the substrate 373 and are capable of reacting to target materials. The plurality of biomolecules 375 may be arranged in a 2D array on the substrate 373. The plurality of biomolecules 375 may include nucleic acids, sugar or sugar binding moieties, or proteins. For example, the biomolecules 375 may include DNA, RNA, aptamers, antigens, antibodies, enzymes, enzyme substrates, enzyme inhibitors, receptors, receptor ligands, or the like.

Although not depicted in the figures, the biochip can further comprise one or more filter portions disposed between at any position between the inlet and outlet of the biochip. For instance, the filter portion can be positioned between the inlet and reactive portion, optionally with one or more fluid resisting portions positioned between the filter and the inlet and/or between the filter and the biochip.

Other aspects of the biochip are as discussed with respect to the fluid controlling apparatus and filter described herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A fluid controlling apparatus comprising:
   an inlet through which a fluid is introduced;
   a channel portion connected to the inlet;
   an outlet connected to the channel portion and through which the fluid is discharged;
   at least one fluid resisting portion disposed between the inlet and the outlet, the at least one fluid resisting portion allowing fluid flow around the fluid resisting portion and only between a surface of the fluid resisting portion and walls defining the channel portion, and wherein the at least one fluid resisting portion is configured to reduce a speed of the fluid and allow stream lines of the fluid to be evenly distributed in the channel portion;
   a filter portion disposed within the channel portion and between the at least one fluid resisting portion and the outlet; and
   a reaction portion disposed within the channel portion to react with target material in the fluid.

2. The fluid controlling apparatus of claim 1, wherein at least one fluid resisting portion has a shape of a diamond, a triangle, a quadrangle, a circle, an oval, a fan shape, or a streamlined shape.

3. The fluid controlling apparatus of claim 1, further comprising:
   a first connecting portion that connects the inlet and the channel portion and having a tapered structure; and
   a second connecting portion that connects the channel portion and the outlet and having a tapered structure.

4. The fluid controlling apparatus of claim 1, wherein a ratio of width to length of the channel portion ranges from 3:1 to 100:1.

5. The fluid controlling apparatus of claim 1, wherein the filter portion comprises a plurality of filter units.

6. The fluid controlling apparatus of claim 5, wherein each of the plurality of filter units comprises:
   a first portion comprising a first plurality of protrusions protruding in a first direction; and
   a second portion spaced apart from and facing the first portion, the second portion comprising a second plurality of protrusions protruding toward the first portion and corresponding to the first plurality of protrusions.

7. The fluid controlling apparatus of claim 6, wherein each of the plurality of filter units further comprises:
   a third portion disposed between the first portion and the second portion;
   a first fluid discharge channel located between the first portion and the third portion; and
   a second fluid discharge channel located between the second portion and the third portion.

8. The fluid controlling apparatus of claim 6, wherein the plurality of filter units are arranged as a plurality of filter sequences.

9. The fluid controlling apparatus of claim 1 wherein the at least one fluid resisting portion is disposed between the inlet and the reaction portion, between the reaction portion and the outlet, or both.

10. The fluid controlling apparatus of claim 1 wherein the reaction portion comprises a plurality of biomolecules.

11. The fluid controlling apparatus of claim 10, wherein the plurality of biomolecules are arranged in a two-dimensional array.

12. The fluid controlling apparatus of claim 10, wherein the plurality of biomolecules comprise nucleic acids, sugars, proteins, or a combination thereof.

13. The fluid controlling apparatus of claim 1, wherein a width of the channel portion is greater than a length of the channel portion.

* * * * *